(12) United States Patent
Ohtani

(10) Patent No.: US 7,968,849 B2
(45) Date of Patent: Jun. 28, 2011

(54) POSITRON CT APPARATUS

(75) Inventor: Atsushi Ohtani, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 227 days.

(21) Appl. No.: 12/375,445

(22) PCT Filed: Jul. 11, 2007

(86) PCT No.: PCT/JP2007/063826
§ 371 (c)(1),
(2), (4) Date: Jan. 28, 2009

(87) PCT Pub. No.: WO2008/018264
PCT Pub. Date: Feb. 14, 2008

(65) Prior Publication Data
US 2009/0309031 A1 Dec. 17, 2009

(30) Foreign Application Priority Data
Aug. 8, 2006 (JP) .................................. 2006-215981

(51) Int. Cl.
G01T 1/161 (2006.01)
(52) U.S. Cl. ................................................. 250/363.03
(58) Field of Classification Search ............... 250/363.03
See application file for complete search history.

(56) References Cited

U.S. PATENT DOCUMENTS

| 5,608,221 A * | 3/1997 | Bertelsen et al. ......... 250/363.03 |
| 6,175,116 B1 * | 1/2001 | Gagnon et al. ........... 250/363.03 |
| 6,294,788 B1 | 9/2001 | Cooke et al. |
| 6,858,850 B2 * | 2/2005 | Williams et al. ......... 250/363.09 |
| 7,045,789 B2 | 5/2006 | Ogawa et al. |
| 2003/0062482 A1 * | 4/2003 | Williams et al. ......... 250/363.03 |
| 2004/0159791 A1 * | 8/2004 | Hefetz ...................... 250/363.03 |
| 2006/0138315 A1 * | 6/2006 | Williams et al. ........... 250/252.1 |
| 2007/0152162 A1 * | 7/2007 | Griesmer et al. ......... 250/363.09 |

FOREIGN PATENT DOCUMENTS

| JP | 07-113873 A | 5/1995 |
| JP | 2000-028727 A | 1/2000 |
| JP | 2001-356172 A | 12/2001 |
| JP | 2002-116256 A | 4/2002 |
| JP | 2007-225393 A | 9/2007 |

OTHER PUBLICATIONS

International Search Report for the Application No. PCT/JP2007/063826 mailed Oct. 2, 2007.

* cited by examiner

*Primary Examiner* — Constantine Hannaher
(74) *Attorney, Agent, or Firm* — Cheng Law Group, PLLC

(57) ABSTRACT

Whether a phenomenon of photon incidence on detectors is a double event or a single event is determined (step S1). When it is a double event, emission data is collected (S2), and is put to an image reconstruction process (S3). When it is a single event, on the other hand, the data is collected as data for calibration (S4), and is put to a calibration process (S5). Since the data for calibration is collected during a clinical practice, a PET apparatus can be calibrated frequently without lowering the operating ratio of the apparatus.

2 Claims, 7 Drawing Sheets

POSITRON CT APPARATUS

TECHNICAL FIELD

This invention relates to a positron CT apparatus (Positron Emission Computed-Tomography: hereinafter also called "PET apparatus"), and more particularly to calibration of energy information in a plurality of detectors provided for a PET apparatus for detecting photons such as gamma rays (Energy Calibration), and calibration of output timing of information on the time when each detector has detected a photon (Time Calibration).

BACKGROUND ART

In a PET apparatus, numerous detectors first detect pair annihilation photons of 511 keV which are positrons generating from a patient administered with a positron-emitting radionuclide, combining with adjacent electrons and emitted in directions of 180 degrees. When two detectors detect photons within a definite period of time, they are counted as one pair of annihilation photons, and it is determined that a pair annihilation generating point exists on a straight line linking the detector pair having detected them. Such coincidence information is accumulated, and an image reconstruction process is carried out to create a positron-emitting radionuclide distribution image (RI distribution image).

However, when scattered pair annihilation photons are counted as a coincidence (hereinafter also called "scatter coincidence"), a true pair annihilation generating point is not on the line linking the detector pair having detected them. The scatter coincidence, therefore, lowers the image quality of a reconstruction image. Thus, image quality is improved by estimating scattered components using measured photon energy information, and deducting them when carrying out a reconstruction process (see Patent Documents 1-3, for example).

[Patent Document 1]
Unexamined Patent Publication H7-113873
[Patent Document 2]
Unexamined Patent Publication No. 2001-356172
[Patent Document 3]
Unexamined Patent Publication No. 2000-28727

DISCLOSURE OF THE INVENTION

Problem to be Solved by the Invention

However, the conventional example with such a construction has the following problem.

Generally, detection outputs of the detectors provided for the PET apparatus for photon detection are variable with ambient temperature and humidity. Therefore, a major air-conditioning control is desired for a PET examination room. Also, an around-the-clock power supply is recommended for the PET apparatus. Further, in order to cope with output variations due to noise variations, variations with time and so on, measurement is carried out every fixed period for energy calibration or time calibration.

The energy calibration is an operation to adjust and uniform gains and offsets of the numerous detectors for photon detection. Each detector gives an analog energy output proportional to the energy of an incident photon. The energy of a photon emitted from a radionuclide used in PET examination is 511 keV. Therefore, the energy of many photons counted as coincidences is 511 keV. On the other hand, among the photons counted as coincidences, also photons acting as noise components are counted as scatter coincidences. The energy values of the photons acting as the noise components are lower than the energy value of the photons counted as true coincidences. Thus, an energy threshold value is set to the energy outputs of the photons counted as coincidences in the detectors, those having energy outputs exceeding this energy threshold value are regarded as true coincidences, and those less than the energy threshold value are eliminated as noise components. However, when the gain and offset of each detector vary, data which should be collected as true coincidences will be discarded vainly, or noise components will mix into the data which should be collected as true coincidences. It is therefore important to carry out energy calibration for each detector for obtaining a good RI distribution image.

The energy calibration of the conventional apparatus is carried out as follows. Data for calibration (coincidence data) is collected using a phantom for energy calibration. And an energy spectrum of photons is collected for each detector. The gain of each detector is adjusted so that the peak in each energy spectrum may become 511 keV. Noise components included in the energy output of each detector are estimated separately, to adjust the offset of each detector.

However, with the energy calibration of the conventional apparatus noted above, the PET apparatus cannot be used for routine diagnosis during the calibration. This poses a problem of lowering the operating efficiency of the apparatus.

On the other hand, the time calibration is an operation to uniform, among the detectors, output timing of time information (pulse signals) outputted when the detectors detect photons. This increases the accuracy of a time window for determining incidences, to cut out random coincidence events. A TOF (time of flight) type PET apparatus measures differences in detection time of annihilation photons counted as coincidences, to determine emission locations of the photons. In such an apparatus, the output timing of time information (pulse signals) outputted when the detectors detect photons is uniform among the detectors. Moreover, when the absolute accuracy of time lag measurement is not good, the detecting accuracy of emission locations of the photons will worsen to lower image quality. It is therefore important to carry out time calibration for each detector for obtaining a good RI distribution image.

The time calibration of the conventional apparatus is carried out as follows. Data for calibration (coincidence data) is collected using a phantom for time calibration. And a time spectrum of photons is collected for each detector, and each is compared with the others, to adjust output timing of the time information (pulse signals) of each detector so that the peak of true coincidences in the spectrum may be uniform.

However, with the time calibration of the conventional apparatus noted above, the PET apparatus cannot be used for routine diagnosis during the calibration. This poses a problem of lowering the operating efficiency of the apparatus. In addition, even if the time calibration uniforms the output timing of the time information (pulse signals) among the detectors, the absolute accuracy of time lag measurement is not guaranteed. Thus, the calibration cannot be said to have sufficiently high precision.

This invention has been made having regard to the state of the art noted above, and its object is to provide a PET apparatus which can carry out calibration without lowering the operating ratio of the PET apparatus, and yet with high accuracy.

Means for Solving the Problem

To fulfill this object, this invention provides the following construction.

A positron CT apparatus of this invention comprises (A) a plurality of detecting devices for detecting photons emitted from a radionuclide given to a patient; (B) an analog-to-digital converter for converting an analog energy output which is one of detection outputs of each detecting device, into digital information of a predetermined number of channels; (C) an event determining device for receiving the detection outputs of each detecting device, and determining whether an event which is a phenomenon of photon incidence on the detecting device serving as a trigger for the detecting device to generate the detection outputs is a double event which is a phenomenon of an annihilation pair of photons being incident on a pair of detecting devices simultaneously, or it is a single event which is a phenomenon of a single photon being incident on a single detecting device; (D) a double event energy information storage device for taking in and accumulating output information of the analog-to-digital converter at the time when the event determining device determines that a certain event is a double event; (E) a single event energy information storage device for taking in output information of the analog-to-digital converter at the time when the event determining device determines that a certain event is a single event, and accumulating for each detecting device an energy channel spectrum expressing a distribution of counts of incident photons relating to the single event on an energy channel axis; (F) an energy peak detecting device for reading, at an appropriate time, the energy channel spectrum of each detecting device accumulated in the single event energy information storage device, and detecting an energy base peak corresponding to a noise level of a background and a self-energy peak peculiar to the radionuclide; (G) an energy conversion factor calculating device for calculating, for each detecting device, an energy conversion factor which is the number of channels per unit energy from a relationship between the number of channels corresponding to an energy interval between the energy base peak and the self-energy peak detected for each detecting device, and an energy value peculiar to the radionuclide; (H) an offset energy detecting device for determining the number of channels corresponding to an offset energy of each detecting device based on a position of the energy base peak of each detecting device; and (I) an energy calibration device for adjusting a gain and an offset of each detecting device and/or an energy channel axis and an offset of the analog-to-digital converter based on the energy conversion factor and the offset energy of each detecting device.

The positron CT apparatus of this invention concerns energy calibration. The characteristics of the energy calibration according to this invention lie in that data for calibration is collected during a clinical time, and that single event data during the clinical time which was discarded by a conventional apparatus is used as the data for calibration. Specifically, photons emitted from the radionuclide given to the patient during a clinical time are detected by the plurality of detecting devices. Each detecting device outputs analog energy outputs according to the energy of incident photons. These analog energy outputs are given to the analog-to-digital converter and the event determining device. The analog-to-digital converter converts the analog energy output into digital information of a predetermined number of channels. On the other hand, the event determining device determines whether an event which is a phenomenon of photon incidence on a detecting device serving as a trigger for the detecting device to generate the detection outputs is a double event which is a phenomenon of an annihilation pair of photons being incident on a pair of detecting devices simultaneously, or it is a single event which is a phenomenon of a single photon being incident on a single detecting device. When the event determining device determines that a certain event is a double event, the double event energy information storage device takes in and accumulates output information of the analog-to-digital converter at that time. This data is used as emission data for reconstruction of an RI distribution image.

When the event determining device determines that a certain event is a single event, on the other hand, the single event energy information storage device takes in output information of the analog-to-digital converter at that time, and collects and accumulates for each detecting device an energy channel spectrum expressing a distribution of counts of incident photons relating to the single event on an energy channel axis. The data relating to the single event is used as calibration data as described hereinafter. First, the energy peak detecting device reads, at an appropriate time, the energy channel spectrum of each detecting device accumulated in the single event energy information storage device, and detects an energy base peak corresponding to a noise level of a background and a self-energy peak peculiar to the radionuclide. The energy base peak corresponds to a state where the energy of the incident photon is zero. The number of channels corresponding to the interval from the energy base peak to the self-energy peak corresponds to the energy peculiar to the radionuclide (511 keV). The amount of shift from the zero channel of the energy base peak corresponds to an offset. Therefore, the energy conversion factor calculating device calculates, for each detecting device, an energy conversion factor which is the number of channels per unit energy from a relationship between the number of channels corresponding to an energy interval between the energy base peak and the self-energy peak detected for each detecting device, and an energy value peculiar to the radionuclide. The offset energy detecting device determines the number of channels corresponding to an offset energy of each detecting device based on a position of the energy base peak of each detecting device. And the energy calibration device adjusts a gain and an offset of each detecting device and/or an energy channel axis and an offset of the analog-to-digital converter based on the energy conversion factor and the offset energy of each detecting device.

Further, a positron CT apparatus of this invention comprises (J) a plurality of detecting devices for detecting photons emitted from a radionuclide given to a patient; (K) a time-to-digital converter for converting information about a time at which a photon is detected, which is one of detection outputs of each detecting device, into digital information of a predetermined number of channels; (L) an event determining device for receiving the detection outputs of each detecting device, and determining whether an event which is a phenomenon of photon incidence on the detecting device serving as a trigger for the detecting device to generate the detection outputs is a double event which is a phenomenon of an annihilation pair of photons being incident on a pair of detecting devices simultaneously, or it is a single event which is a phenomenon of a single photon being incident on a single detecting device; (M) a double event time information storage device for taking in and accumulating output information of the time-to-digital converter at the time when the event determining device determines that a certain event is a double event; (N) a single event time information storage device for taking in, at a time when the event determining device determines that a certain event is a single event, the information about the time at which a photon is detected, and information about a time taken until the certain event is determined to be a single event, from the time-to-digital converter, and accumulating for each detecting device a time channel spectrum expressing a distribution of counts of incident photons relating to the single event on a time channel axis; (O) a time peak detecting device for reading, at an appropriate time, the time channel spectrum of each detecting device accumulated in the single event time information storage device, and detecting a time base peak corresponding to the time at which a photon is detected and a determination time peak corresponding to the time taken until the certain event is determined to be a single event; (P) a time conversion factor calculating device for calculating, for each detecting device, a time conversion factor which is the number of channels per unit time from a relationship between the number of channels corresponding to a time interval between the time base peak and the determination time peak detected for each detecting device, and a reference determination time which is a predetermined maximum incidence time lag of annihilation pair photons; (Q) an offset time detecting device for determining the number of channels corresponding to an offset time of each detecting device based on a position of the time base peak of each detecting device; and (R) a time calibration device for adjusting a time axis and an offset of the time-to-digital converter corresponding to each detecting device based on the time conversion factor and the offset time of each detecting device.

The positron CT apparatus of this invention concerns time calibration. The characteristics of the time calibration according to this invention, as do those of the energy calibration noted above, lie in that data for calibration is collected during a clinical time, and that single event data during the clinical time which was discarded by a conventional apparatus is used as the data for calibration. Specifically, photons emitted from a radionuclide given to the patient during a clinical time are detected by the plurality of detecting devices. Each detecting device outputs information about a time at which a photon is detected as one of detection outputs. This information about the time is given to the time-to-digital converter and the event determining device. The time-to-digital converter converts the information about the time at which a photon is detected into digital information of a predetermined number of channels. On the other hand, the event determining device determines whether an event which is a phenomenon of photon incidence on a detecting device serving as a trigger for the detecting device to generate the detection outputs is a double event which is a phenomenon of an annihilation pair of photons being incident on a pair of detecting devices simultaneously, or it is a single event which is a phenomenon of a single photon being incident on a single detecting device. When the event determining device determines that a certain event is a double event, the double event time information storage device takes in and accumulates output information of the time-to-digital converter at that time. This data is used as emission data for reconstruction of an RI distribution image.

When the event determining device determines that a certain event is a single event, on the other hand, the single event time information storage device takes in the information about the time at which a photon is detected, and information about a time taken until the certain event is determined to be a single event, from the time-to-digital converter, and accumulates for each detecting device a time channel spectrum expressing a distribution of counts of incident photons relating to the single event on a time channel axis. The data relating to the single event is used as calibration data as described hereinafter. First, the time peak detecting device reads, at an appropriate time, the time channel spectrum of each detecting device accumulated in the single event time information storage device, and detects a time base peak corresponding to the time of detecting a photon and a determination time peak corresponding to the time taken until the certain event is determined to be a single event. The time base peak corresponds to the time when the detecting device detected a photon. The number of channels corresponding to the interval from the time base peak to the determination time peak corresponds to a reference determination time which is a maximum incidence time lag of annihilation pair photons set beforehand in order to determine whether a certain event is a double event or a single event. The amount of shift from the zero channel of the time base peak corresponds to an offset. Therefore, the time conversion factor calculating device calculates, for each detecting device, a time conversion factor which is the number of channels per unit time from a relationship between the number of channels corresponding to a time interval between the time base peak and the determination time to peak detected for each detecting device, and the reference determination time which is a maximum incidence time lag of annihilation pair photons set beforehand in order to determine whether a certain event is a double event or a single event. The offset time detecting device determines the number of channels corresponding to an offset time of each detecting device based on a position of the time base peak of each detecting device. And the time calibration device adjusts a time axis and an offset of the time-to-digital converter corresponding to each detecting device based on the time conversion factor and the offset time of each detecting device.

Effects of the Invention

The positron CT apparatus according to this invention collects calibration data during a clinical time without the need to carry out a special data collecting operation using a phantom or the like in order to collect calibration data. It is therefore possible to shorten a period for stopping the PET apparatus for calibration, thereby to improve the operating efficiency of the apparatus. Since calibration data is collected for each clinical practice to enable frequent calibrations of the PET apparatus, the PET apparatus is maintainable with high precision. Further, data (emission data) relating to a double event used for clinical purposes and data relating to a single event which is generally discarded without being used for clinical purposes is collected in parallel. Since calibration is carried out using the data relating to the single event which provides a relatively large amount of data, the apparatus can be calibrated efficiently. Especially the former invention concerning the energy calibration can calibrate the energy information of each detecting device with high accuracy. The latter invention concerning the time calibration can calibrate the time information of each detecting device with high accuracy.

DESCRIPTION OF REFERENCES

Figure 1:
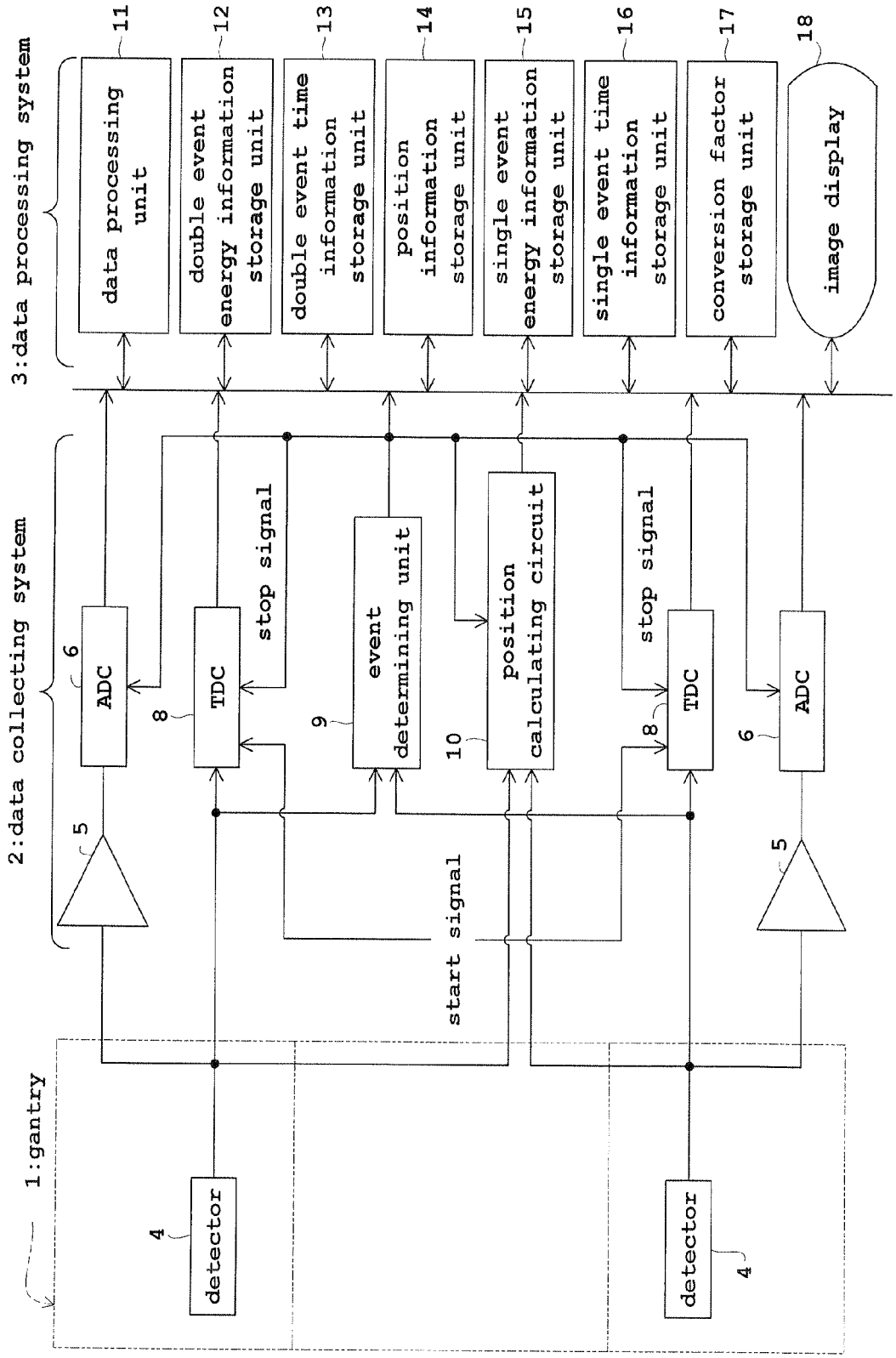
FIG. 1 is a block showing an outline of a PET apparatus in one embodiment of this invention.

4 . . . detectors
5 . . . amplifiers
6 . . . analog-to-digital converters (ADCs)
8 . . . time-to-digital converters (TDCs)
9 . . . event determining unit
10 . . . position calculating circuit
11 . . . data processing unit
12 . . . double event energy information storage unit
13 . . . double event time information storage unit
14 . . . position information storage unit
15 . . . single event energy information storage unit
16 . . . single event time information storage unit
17 . . . conversion factor storage unit

EMBODIMENT

An embodiment of this invention will be described hereinafter with reference to the drawings.

FIG. 1 is a block diagram showing a principal portion of a PET apparatus according to the embodiment.

The PET apparatus according to this embodiment is roughly divided into a gantry 1, a data collecting system 2 and a data processing system 3. The gantry 1 includes a plurality of detectors 4 for detecting photons emitted from a radionuclide given to a patient. The detectors 4 have scintillators (not shown) for converting the photons into visible light, and photomultiplier tubes (not shown) for converting the visible light into electric signals. The plurality of such detectors 4 are arranged in order in a ring form around the opening of gantry 1 in which the patient is inserted. However, FIG. 1 shows only two detectors 4 for expediency of illustration.

The data collecting system 2 is a system for collecting energy information of the photons detected by the detectors 4, information about the time at which the photons are detected, and information about incident positions of the photons. Specifically, an analog energy output which is one of the detection outputs of each detector 4 is given to an analog-to-digital converter (ADC) 6 through an amplifier 5. The ADC 6 converts the inputted analog energy signal into digital information corresponding to a predetermined number of channels (128 channels in this embodiment).

The information about the time at which a photon is detected (pulse signal generated by photon incidence) which is one of the detection outputs of each detector 4 is given to a time-to-digital converter (TDC) 8. The TDC 8 converts the information about the time at which the photons are detected into digital information (digital time output) corresponding to the predetermined number of channels (128 channels in this embodiment).

A start signal is given commonly to the TDC 8 of each detector 4. A stop signal is given to the TDC 8 from an event determining unit 9 described hereinafter. The start signal may be a signal from the detector 4, or may be a signal synchronized with a master clock which carries out overall control of the entirety.

Further, the information about the time at which the photons are detected, outputted from each detector 4, is given to the event determining unit 9. The event determining unit 9 determines whether an event which is an incidence phenomenon of photons on each detector 4 serving as a trigger for the detector 4 to generate the detection output is a double event which is a phenomenon of an annihilation pair of photons being incident on a pair of detectors 4 simultaneously, or a single event which is a phenomenon of a single photon being incident on a single detector 4.

The event determining unit 9 has, set thereto, a reference determination time which is a predetermined maximum incidence time lag of an annihilation pair of photons, in order to determine whether a certain event is a double event or a single event. In this embodiment, 10 nanoseconds is set as the reference determination time Therefore, when following photon incidence time information is received within 10 nanoseconds after the information about the time at which a photon is detected (photon incidence time information) is received by the event determining unit 9 first, that event is determined to be a double event (true coincidence). Conversely, if following photon incidence time information is not received within 10 nanoseconds, the first photon incidence time information is determined to be a single event. Such results of determination are given to the ADC 6 and TDC 8 and a position calculating circuit 10 described hereinafter. The above stop signal, in particular, is given to the TDC 8.

The detection output of each detector 4 is given to the position calculating circuit 10. The position calculating circuit 10 calculates incident positions of the photons from the ratio of the detection output of each detector 4 when the incidence phenomenon of the photons is determined to be a double event.

The data processing system 3 will be described. The data processing system 3 includes a data processing unit 11 in the form of a computer. The data processing unit 11 reconstructs RI distribution images based on emission data stored (data collected by double events), and performs a calibration process which is the characteristic of the apparatus in this embodiment. The data processing system 3 further includes a double event energy information storage unit 12, a double event time information storage unit 13 and a position information storage unit 14 as elements for storing data produced by double events for image reconstruction. The data processing system 3 also includes a single event energy information storage unit 15, a single event time information storage unit 16 and a conversion factor storage unit 17 as elements for storing data produced by single events in order to carry out calibration.

The double event energy information storage unit 12 accumulates digital energy information which is the output of ADC 6 at a time when the event determining unit 9 determines that the incidence phenomenon of photons is a double event. The double event time information storage unit 13 accumulates digital time information which is the output of TDC 8 at the time of a double event. The position information storage unit 14 accumulates photon incident position information which is the output of the position calculating circuit 10 at the time of a double event.

The single event energy information storage unit 15, when the event determining unit 9 determines that a photon incidence phenomenon is a single event, takes in the output information of ADC 6 at that time, and accumulates, for each detector 4, an energy channel spectrum (see FIG. 4) which expresses a distribution of counts of incident photons relating to single events on an energy channel axis. The single event time information storage unit 16, when the event determining unit 9 determines that a photon incidence phenomenon is a single event, takes in from the TDC 8 the information about the time at which a photon is detected, and information about the time (10 nanoseconds in this embodiment) taken to determine that a certain event is a single event, and accumulates, for each detector 4, a time channel spectrum (see FIG. 7) which expresses a distribution of counts of incident photons relating to single events on a time channel axis. The conversion factor storage unit 17 temporally accumulates energy conversion factors obtained in the course of an energy calibration process, and time conversion factors obtained in the course of a time calibration process.

In addition, the data processing system 11 includes an image display 18 for displaying reconstructed RI distribution images, data collected in the calibration processes, and so on, and a control input unit not shown.

Operation of the apparatus in this embodiment will be described hereinafter.

<Data Collecting Process>

Figure 2:
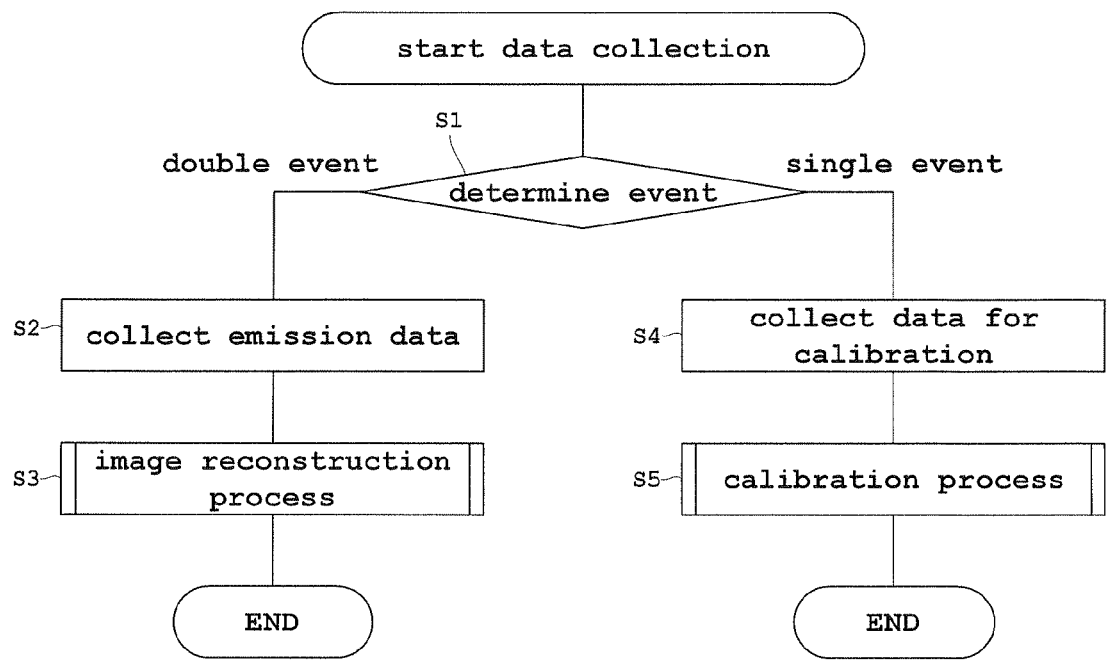
FIG. 2 is a flow chart showing a flow of a data collecting process in the apparatus in the embodiment.

Reference is made to the flow chart of FIG. 2. A patient medicated with a radionuclide during a clinical time is inserted in the opening of gantry 1. Each detector 4 in the gantry 1 detects photons emitted from the radionuclide in the patient. At this time, the event determining unit 9 determines whether the incidence phenomenon of the photons to the detector 4 is a double event or a single event (step S1). When it is determined to be a double event, each data of ADC 6, TDC 8 and position calculating circuit 10 at that time is stored as emission data in the double event energy information storage unit 12, double event time information storage unit 13 and position information storage unit 14 individually (step S2). The emission data stored is put to an image reconstruction process by the data processing unit 11 (step S3). On the other hand, when the event determining unit 9 determines that the photon incidence phenomenon is a single event, each data of ADC 6 and TDC 8 at that time is stored as data for calibration in the single event energy information storage unit 15 and single event time information storage unit 16 individually (step S4). The data for calibration stored is put to a calibration process performed in a timely manner by the data processing unit 11 (step S5). The calibration process which is a characterizing portion of the apparatus in this embodiment will be described hereinafter.

<Energy Calibration Process>

Figure 4:
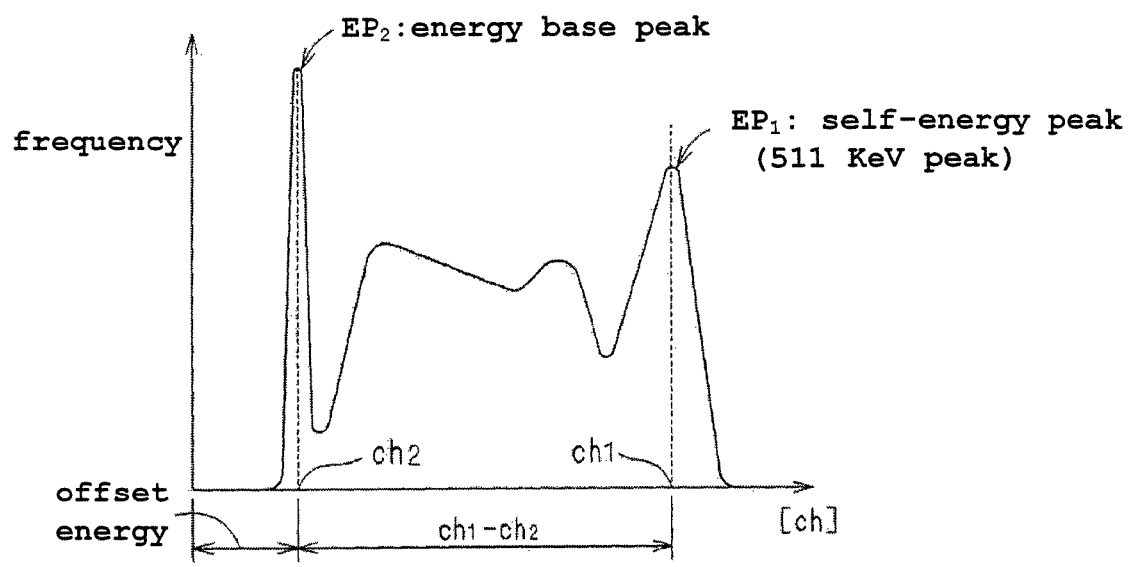
FIG. 4 is a view of an ADC spectrum collected in the course of the energy calibration process.

As noted above, the single event energy information storage unit 16, when the event determining unit 9 determines that a photon incidence phenomenon is a single event, takes in the output information of ADC 6 at that time, and accumulates, for each detector 4, an energy channel spectrum which expresses a distribution of counts of incident photons relating to single events on an energy channel axis. FIG. 4 shows an example of the energy channel spectra collected. In FIG. 4, the horizontal axis is a channel axis (energy channel axis) which is an output unit of ADC 6, and the vertical axis is a single event (photon incidence) frequency. A peak $EP_1$ in the spectrum is a self-energy peak corresponding to the energy value (511 keV) peculiar to the radionuclide. A peak $EP_2$ is an energy base peak corresponding to a noise level in the background.

Figure 3:
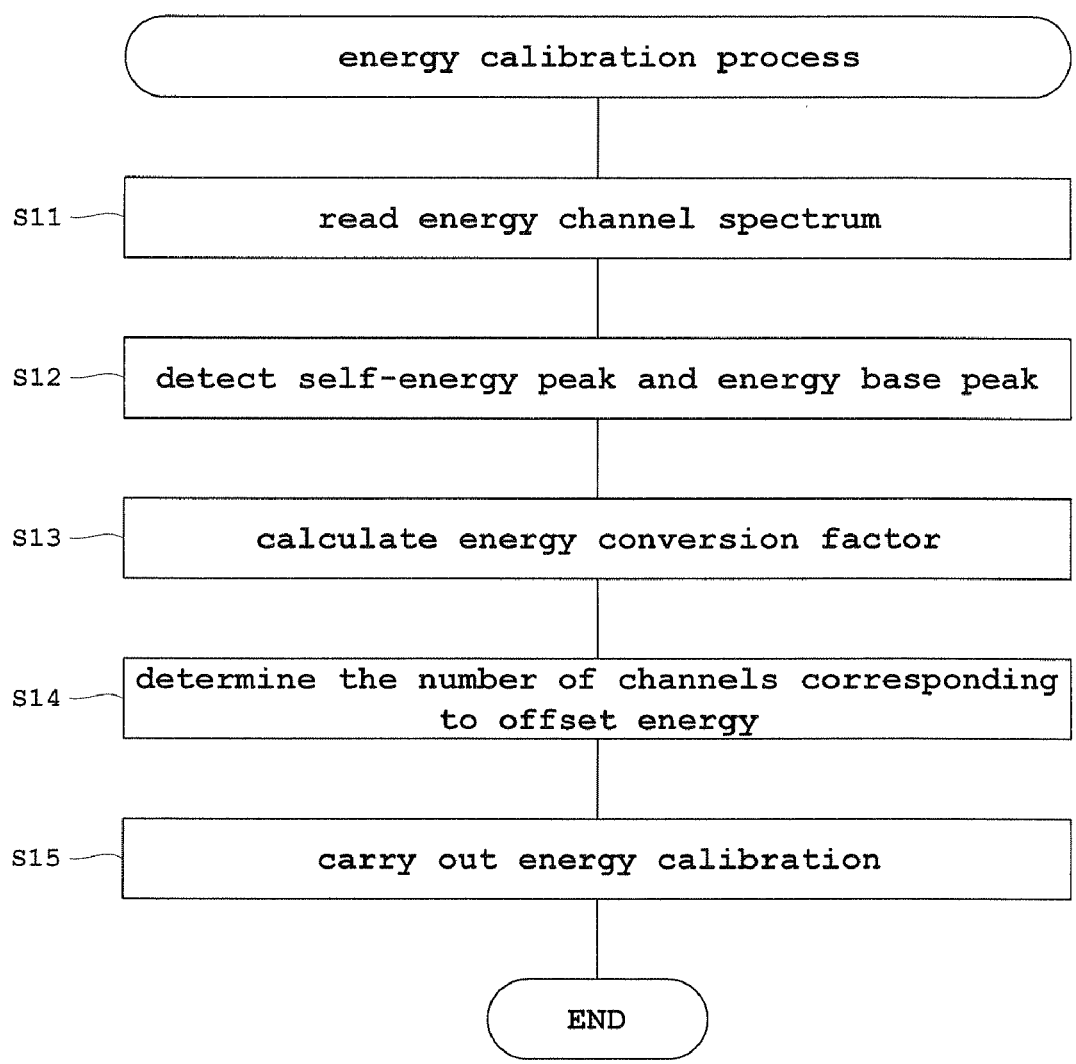
FIG. 3 is a flow chart showing a flow of an energy calibration process.

Description will be made hereinafter with reference to the flow chart of FIG. 3. The energy calibration is carried out when the data processing unit 11 reads an energy channel spectrum from the single event energy information storage unit 15 at an appropriate time (step S11). In this embodiment, calibration data is collected during a clinical time. Thus, calibration can most frequently be carried out at every clinical time, but it may be about once a day.

The data processing unit 11 detects the self-energy peak and energy base peak from the energy channel spectrum read for each detector 4 (step S12). The data processing unit 11 having such a peak detecting function corresponds to the energy peak detecting device of this invention.

The data processing unit 11 calculates, for each detector 4, an energy conversion factor which is the number of channels per unit energy from a relationship between the number of channels corresponding to an energy interval between the energy base peak and self-energy peak detected for each detector 4, and the energy value peculiar to the radionuclide (step S13). The data processor 11 having such an energy conversion factor calculating function corresponds to the energy conversion factor calculating device of this invention. Specifically, the energy conversion factor is calculated from the following equation:

$$\text{energy conversion factor } [ch/keV] = (\text{self-energy peak } [ch] - \text{energy base peak } [ch])/511 \text{ [keV]}$$

As seen from FIG. 4, the number of channels ($ch_1$-$ch_2$) corresponding to the interval between the self-energy peak $ch_1$ and energy base peak $ch_2$ corresponds to the self-energy value (511 keV) of the radionuclide. By dividing the peak interval ($ch_1$-$ch_2$) by 511 keV, the energy conversion factor which is the number of the channels per unit energy can be obtained.

Further, the data processing unit 11 determines the number of channels corresponding to the offset energy of each detector 4 based on the position of energy base peak $EP_2$ of each detector 4 (step S14). The data processing unit 11 having such a function corresponds to the offset energy detecting device of this invention. Specifically, the number of channels which corresponds to the space from 0 ch to the energy base peak $ch_2$ in FIG. 4 is determined. This space is an offset based on the so-called noise of the background.

The data processing unit 11 carries out the energy calibration of each detector 4 using the energy conversion factor and offset energy obtained in this way (step S15). The energy calibration is carried out by adjusting the gain and offset of each detector 4 (specifically, amplifier 5 shown in FIG. 1), and/or the energy channel axis and offset of each ADC 6. This embodiment carries out the latter calibration process with software. This process will be described hereinafter.

In this embodiment, the energy output is calibrated by returning the digital energy output of ADC 6 from the channel unit [ch] to the energy unit [keV], using the energy conversion factor [ch/keV] and offset energy [ch] obtained in steps S13 and S14. Specifically, the energy output [keV] is calibrated by deducting the offset energy [ch] from the digital energy output [ch] of ADC 6, and dividing the difference by the energy conversion factor [ch/keV]. This operation is expressed by the following equation:

$$\text{energy [keV]} = (ADC[ch] - \text{energy base peak } [ch])/\text{energy conversion factor } [ch/keV]$$

Figure 5:
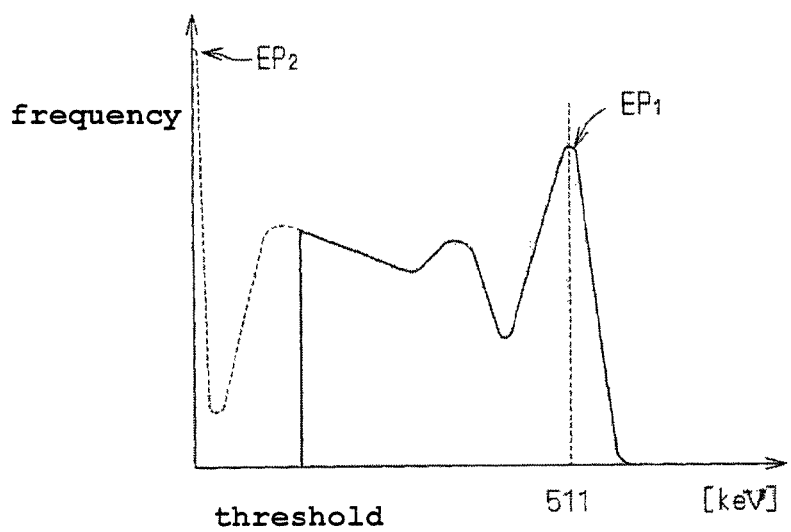
FIG. 5 is a view of an energy spectrum obtained in the energy calibration process.

The energy spectrum calibrated as described above is shown in FIG. 5. As seen from FIG. 5, the offset energy [ch] is deducted from the digital energy output [ch] of ADC 6, and the offset of each detector 4 is calibrated as a result. The noise level of the background after the calibration is uniformed to the reference value (0 keV). By dividing, by the energy conversion factor [ch/keV], the difference resulting from the offset energy [ch] being deducted from the digital energy output [ch] of ADC 6, the gain of each detector 4 is calibrated as a result, and the calibrated energy value peculiar to the radionuclide is uniformed to 511 keV.

<Time Calibration Process>

Figure 7:
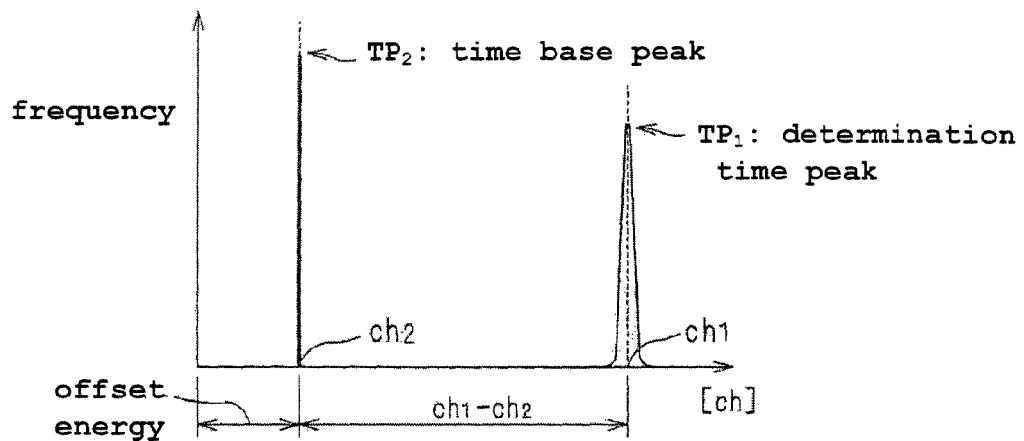
FIG. 7 is a view of a TDC spectrum collected in the course of the time calibration process.

As noted above, the single event time information storage unit 16, when the event determining unit 9 determines that a photon incidence phenomenon is a single event, takes in from the TDC 8 the information about the time at which the photon is detected, and information about the time (10 nanoseconds in this embodiment) taken to determine that a certain event is a single event, and accumulates, for each detector 4, a time channel spectrum which expresses a distribution of counts of incident photons relating to single events on a time channel axis. FIG. 7 shows an example of time channel spectra collected. The horizontal axis is a channel axis (time channel axis) which is an output unit of TDC 8, and the vertical axis is a single event (photon incidence) frequency. A peak $TP_1$ in the spectrum is a determination time peak corresponding to the time (10 nanoseconds in this embodiment) taken to determine that a certain event is a single event. A peak $TP_2$ is a time base peak corresponding to the time at which the photon is detected.

Figure 6:
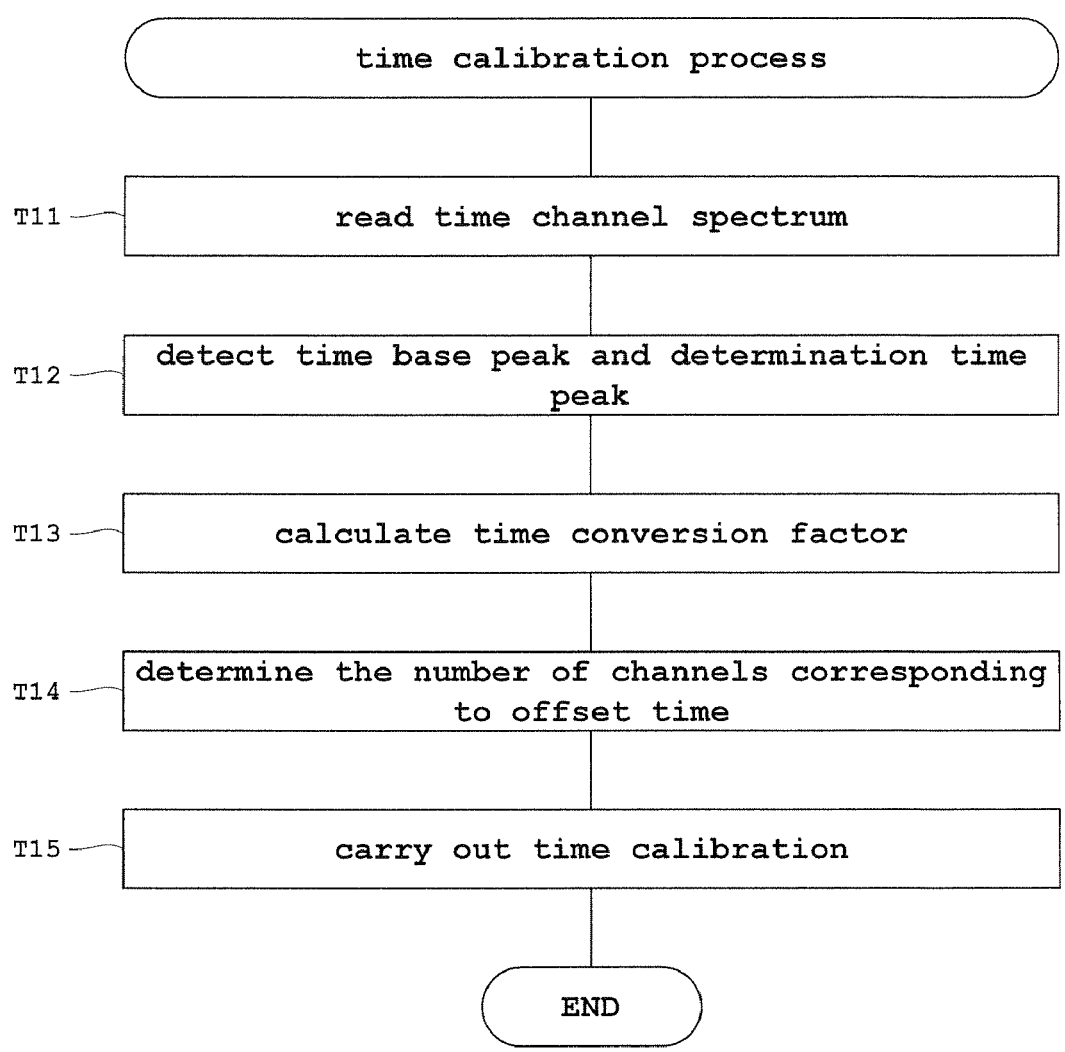
FIG. 6 is a flow chart showing a flow of a time calibration process.

Description will be made hereinafter with reference to the flow chart of FIG. 6. The time calibration is carried out when the data processing unit 11 reads a time channel spectrum from the single event time information storage unit 16 at an appropriate time (step T11).

The data processing unit 11 detects the time base peak and determination time peak from the time channel spectrum read for each detector 4 (step T12). The data processing unit 11 having such a peak detecting function corresponds to the time peak detecting device of this invention.

The data processing unit 11 calculates, for each detector 4, a time conversion factor which is the number of channels per unit time from a relationship between the number of channels corresponding to a time interval between the time base peak and determination time peak detected for each detector 4, and the reference determination time (10 nanoseconds) which is a maximum incidence time lag of annihilation pair photons set beforehand for determining whether a certain event is a double event or a single event (step T14). The data processing unit 11 having such a time conversion factor calculating function corresponds to the time conversion factor calculating device of this invention. Specifically, the time conversion factor is calculated from the following equation:

time conversion factor [$ch$/nanoseconds]=(determination time peak [$ch$]–time base peak [$ch$])/10 [nanoseconds]

Photons are determined to be detected at the time the start signal noted above is given to the TDCs 8. A certain event is determined to be a single event at the time the stop signal is given to the TDCs 8. Where the start signal is a signal from a detector 4, the detector 4 having detected photons outputs the start signal as a trigger given commonly to the TDC 8 of each detector 4. Where the start signal is a signal synchronized with the master clock, the start signal synchronized with the master clock is outputted after a photon is detected, and is given commonly to the TDC 8 of each detector 4. When a certain event is determined to be a single event, the above stop signal is outputted to the TDCs 8. Therefore, the determination time peak [ch]—time base peak [ch] is the output difference between the start signal and stop signal.

As seen from FIG. 7, the number of channels ($ch_1$-$ch_2$) corresponding to the interval between the determination time peak $TP_1$ and time base peak $TP_2$ corresponds to the reference determination time (10 nanoseconds). By dividing the peak interval ($ch_1$-$ch_2$) by the reference determination time (10 nanoseconds), the time conversion factor which is the number of the channels per unit time [nanoseconds] can be obtained.

Further, the data processing unit 11 determines the number of channels corresponding to the offset time of each detector 4 based on the position of the time base peak of each detector 4 (step S14). The data processing unit 11 having such a function corresponds to the offset time detecting device of this invention. Specifically, the number of channels which corresponds to the space from 0 ch to the time base peak $TP_2$ in FIG. 7 is determined.

The data processing unit 11 carries out the time calibration of each detector 4 using the time conversion factor and offset time obtained in this way (step T15). The time calibration is carried out by adjusting the time channel axis and offset of the TDC 8. This process will be described hereinafter.

In this embodiment, the time information of each detector 4 is calibrated by returning the digital time output of TDC 8 from the channel unit [ch] to the time unit [nanoseconds], using the time conversion factor [ch/nanoseconds] and offset time [ch] obtained in steps T13 and T14. Specifically, the time information [nanoseconds] is calibrated by deducting the offset time [ch] from the digital time output [ch] of TDC 8, and dividing the difference by the time conversion factor [ch/nanoseconds]. This operation is expressed by the following equation:

time information [nanoseconds]=(TDC[$ch$]–time base peak [$ch$])/time conversion factor [$ch$/nanoseconds]

Figure 8:
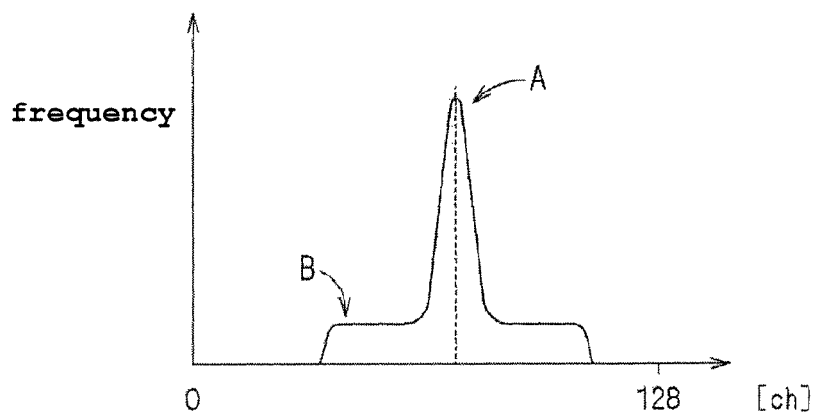
FIG. 8 is a view of a TDC spectrum collected in a double event.
Figure 9:
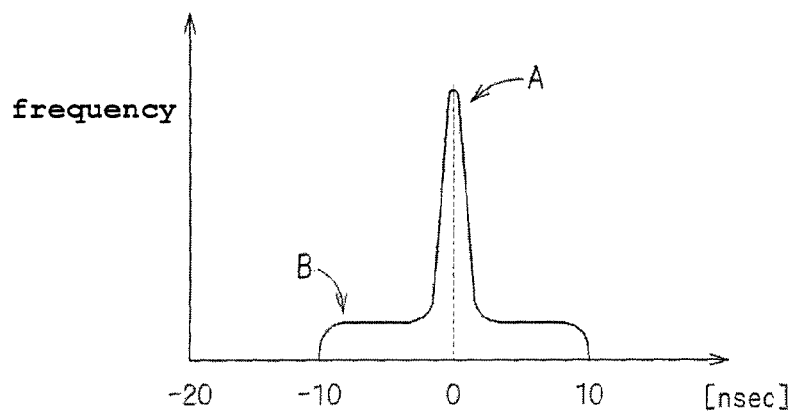
FIG. 9 is a view of a time spectrum obtained in the time calibration process.

FIG. 8 shows a spectrum of time information (digital time output of TDC 8) acquired when a double event is determined. In FIG. 8, peak A in the center is a true coincidence, and skirt areas B are scatter coincidences. Such channel spectrum of TDC 8 corresponding to each detector 4 undergoes the above time calibration process, and becomes a time spectrum as shown in FIG. 9. That is, the channel value of peak A in FIG. 8 shifts to "0" nanoseconds by adjusting of the offset time. The scale of the time axis of the time spectrum corresponding to each detector 4 is uniformed by the division by the time conversion factor.

To determine the time conversion factor and acquire time information by division by the time conversion factor is useful particularly when applied to the TOF (time of flight) type PET apparatus noted hereinbefore. That is, the scale of the time axis of the time spectrum is uniformed by division by the time conversion factor to guarantee the absolute accuracy of time lag measurement. Thus, a difference in detection time of annihilation photons counted as coincidences can be measured with high accuracy.

According to the apparatus in this embodiment, as described above, data (emission data) relating to the double event is collected during a clinical time, and data relating to the single event which generally is discarded without being used for clinical purposes is collected in parallel. Since the calibration is carried out using the data relating to the single event, the apparatus can be calibrated without lowering the operating ratio of the apparatus.

<Detector Abnormality Detection Process>

Figure 10:
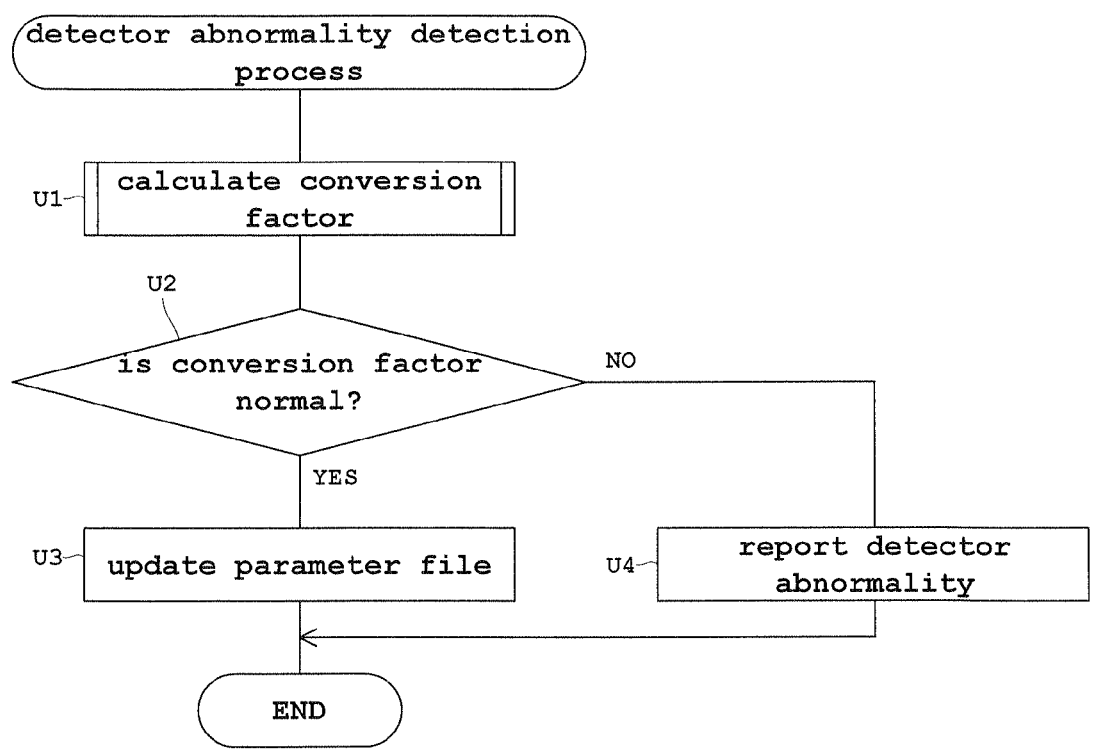
FIG. 10 is a flow chart showing a flow of a detector abnormality detection process.

A detector abnormality of the PET apparatus can be detected using the energy conversion factor or time conversion factor calculated in the course of the above calibration process. This will be described hereinafter with reference to the flow chart of FIG. 10.

When the energy conversion factor or time conversion factor is calculated in step U1, whether the conversion factor is normal or not is determined in the next step U2. Specifically, a conversion factor calculated in a previous calibration process is used as a reference value, and the apparatus is determined abnormal when the conversion factor calculated in the current calibration process is varied by a predetermined value from the reference value. If the conversion factor is normal, the conversion factor is written and stored in a parameter file in the conversion factor storage unit 17 (step U3). On the other hand, if the conversion factor is abnormal, it is determined that an abnormality has occurred with the detector, and this is reported (step U4). Since the conversion factor is calculated for each detector, abnormalities of the numerous detectors can be discovered easily by monitoring variations of the conversion factor.

The reference value for determining whether the conversion factor is normal or abnormal, preferably, is prepared from a short-term comparison (e.g. at each examination), a mid-term comparison (e.g. daily) or a long-term comparison (e.g. weekly), by referring to the parameter file in the conversion factor storage unit 17 which records the conversion factor temporally. The ADC spectrum (FIG. 4) or TDC spectrum (FIG. 7) obtained from each calibration process may be displayed on the image display 18 to enable a visual evaluation whether each calibration is appropriate.

The invention claimed is:

1. A positron CT apparatus comprising (A) a plurality of detecting devices for detecting photons emitted from a radionuclide given to a patient; (B) an analog-to-digital converter for converting an analog energy output which is one of detection outputs of each detecting device, into digital information of a predetermined number of channels; (C) an event determining device for receiving the detection outputs of each detecting device, and determining whether an event which is a phenomenon of photon incidence on the detecting device serving as a trigger for the detecting device to generate the detection outputs is a double event which is a phenomenon of an annihilation pair of photons being incident on a pair of detecting devices simultaneously, or it is a single event which is a phenomenon of a single photon being incident on a single detecting device; (D) a double event energy information storage device for taking in and accumulating output information of the analog-to-digital converter at the time when the event determining device determines that a certain event is a double event; (E) a single event energy information storage device for taking in output information of the analog-to-digital converter at the time when the event determining device determines that a certain event is a single event, and accumulating for each detecting device an energy channel spectrum expressing a distribution of counts of incident photons relating to the single event on an energy channel axis; (F) an energy peak detecting device for reading, at an appropriate time, the energy channel spectrum of each detecting device accumulated in the single event energy information storage device, and detecting an energy base peak corresponding to a noise level of a background and a self-energy peak peculiar to the radionuclide; (G) an energy conversion factor calculating device for calculating, for each detecting device, an energy conversion factor which is the number of channels per unit energy from a relationship between the number of channels corresponding to an energy interval between the energy base peak and the self-energy peak detected for each detecting device, and an energy value peculiar to the radionuclide; (H) an offset energy detecting device for determining the number of channels corresponding to an offset energy of each detecting device based on a position of the energy base peak of each detecting device; and (I) an energy calibration device for adjusting a gain and an offset of each detecting device and/or an energy channel axis and an offset of the analog-to-digital converter based on the energy conversion factor and the offset energy of each detecting device.

2. A positron CT apparatus comprising (J) a plurality of detecting devices for detecting photons emitted from a radionuclide given to a patient; (K) a time-to-digital converter for converting information about a time at which a photon is detected, which is one of detection outputs of each detecting device, into digital information of a predetermined number of channels; (L) an event determining device for receiving the detection outputs of each detecting device, and determining whether an event which is a phenomenon of photon incidence on the detecting device serving as a trigger for the detecting device to generate the detection outputs is a double event which is a phenomenon of an annihilation pair of photons being incident on a pair of detecting devices simultaneously, or it is a single event which is a phenomenon of a single photon being incident on a single detecting device; (M) a double event time information storage device for taking in and accumulating output information of the time-to-digital converter at the time when the event determining device determines that a certain event is a double event; (N) a single event time information storage device for taking in, at a time when the event determining device determines that a certain event is a single event, the information about the time at which a photon is detected, and information about a time taken until the certain event is determined to be a single event, from the time-to-digital converter, and accumulating for each detecting device a time channel spectrum expressing a distribution of counts of incident photons relating to the single event on a time channel axis; (O) a time peak detecting device for reading, at an appropriate time, the time channel spectrum of each detecting device accumulated in the single event time information storage device, and detecting a time base peak corresponding to the time at which a photon is detected and a determination time peak corresponding to the time taken until the certain event is determined to be a single event; (P) a time conversion factor calculating device for calculating, for each detecting device, a time conversion factor which is the number of channels per unit time from a relationship between the number of channels corresponding to a time interval between the time base peak and the determination time peak detected for each detecting device, and a reference determination time which is a predetermined maximum incidence time lag of annihilation pair photons; (Q) an offset time detecting device for determining the number of channels corresponding to an offset time of each detecting device based on a position of the time base peak of each detecting device; and (R) a time calibration device for adjusting a time axis and an offset of the time-to-digital converter corresponding to each detecting device based on the time conversion factor and the offset time of each detecting device.

* * * * *